(12) United States Patent
Haines

(10) Patent No.: US 6,695,848 B2
(45) Date of Patent: Feb. 24, 2004

(54) METHODS FOR FEMORAL AND TIBIAL RESECTION

(75) Inventor: Timothy G. Haines, New Brighton, MN (US)

(73) Assignee: Hudson Surgical Design, Inc., New Brighton, NJ (US)

( * ) Notice: Subject to any disclaimer, the term of this patent is extended or adjusted under 35 U.S.C. 154(b) by 0 days.

(21) Appl. No.: 09/799,325

(22) Filed: Mar. 5, 2001

(65) Prior Publication Data

US 2002/0029038 A1 Mar. 7, 2002

Related U.S. Application Data

(63) Continuation-in-part of application No. 09/261,528, filed on Mar. 3, 1999, now Pat. No. 6,197,064, which is a continuation of application No. 08/892,286, filed on Jul. 14, 1997, now Pat. No. 5,879,354, which is a division of application No. 08/649,465, filed on May 17, 1996, now Pat. No. 5,755,803, which is a continuation-in-part of application No. 08/603,582, filed on Feb. 20, 1996, now Pat. No. 5,810,827, which is a continuation-in-part of application No. 08/300,379, filed on Sep. 2, 1994, now Pat. No. 5,514,139, said application No. 08/603,582, is a continuation-in-part of application No. 08/479,363, filed on Jun. 7, 1995, now Pat. No. 5,643,272, which is a continuation of application No. 08/342,143, filed on Nov. 18, 1994, now Pat. No. 5,597,379, which is a continuation-in-part of application No. 08/300,379, said application No. 08/479,363, is a continuation-in-part of application No. 08/300,379, said application No. 08/603,582, is a continuation-in-part of application No. 08/342,143.

(51) Int. Cl.[7] .............................................. A61B 17/16
(52) U.S. Cl. ....................................................... 606/79
(58) Field of Search .............................. 606/79, 80, 86, 606/87, 88, 89, 96, 98

(56) References Cited

U.S. PATENT DOCUMENTS

| | | | | |
|---|---|---|---|---|
| 3,739,662 A | * | 6/1973 | Windelman et al. | 76/107 R |
| 4,841,975 A | * | 6/1989 | Woolson | 128/653 |
| 5,021,056 A | * | 6/1991 | Hofmann et al. | 606/86 |
| 5,263,498 A | * | 11/1993 | Caspari et al. | 128/898 |
| 5,454,816 A | * | 10/1995 | Ashby | 606/88 |
| 5,980,526 A | * | 11/1999 | Johnson et al. | 606/86 |

* cited by examiner

Primary Examiner—Eduardo C. Robert
(74) Attorney, Agent, or Firm—Patterson, Thuente, Skaar & Christensen, P.A.

(57) ABSTRACT

Methods and apparatus for femoral and tibial resection are provided. The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A modified cutting guide can be used to position a conventional cutting block against a femur to be resected.

1 Claim, 25 Drawing Sheets

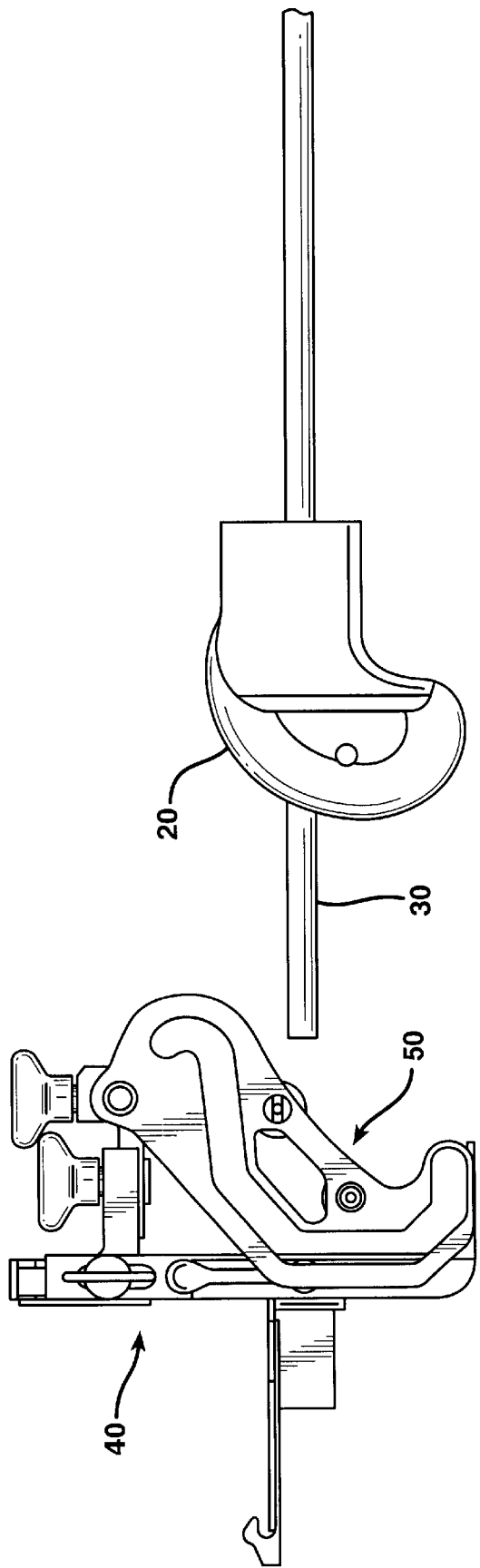

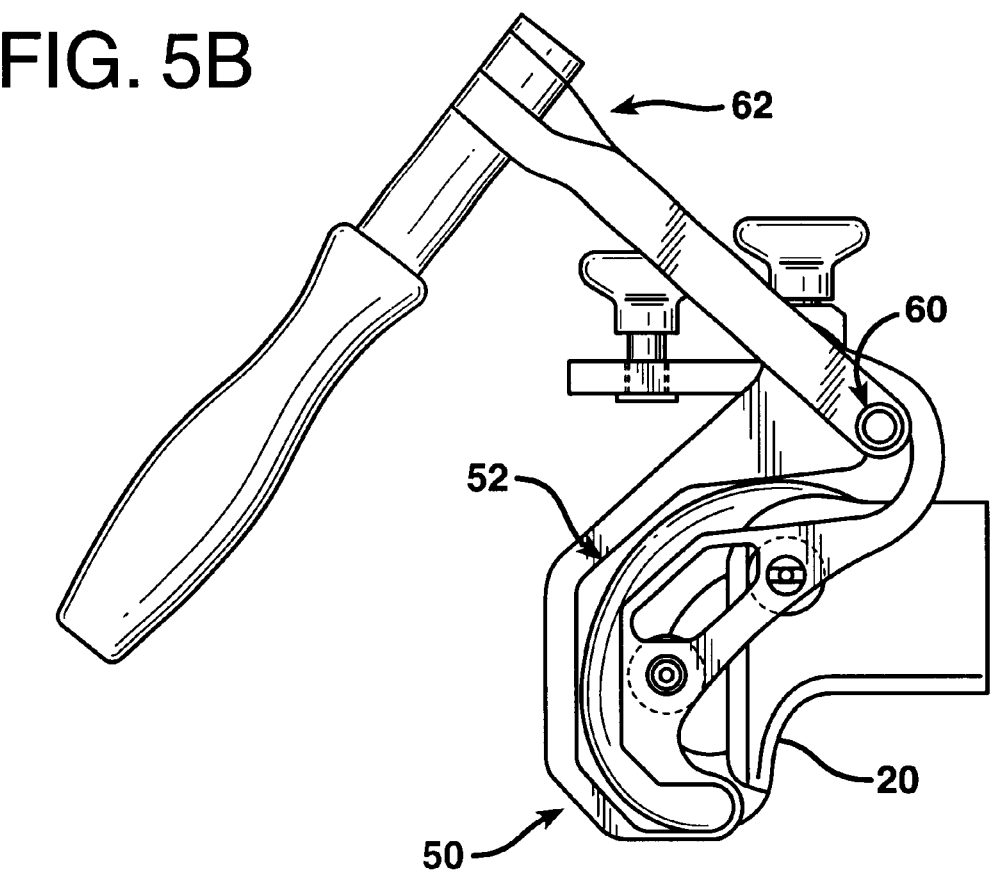

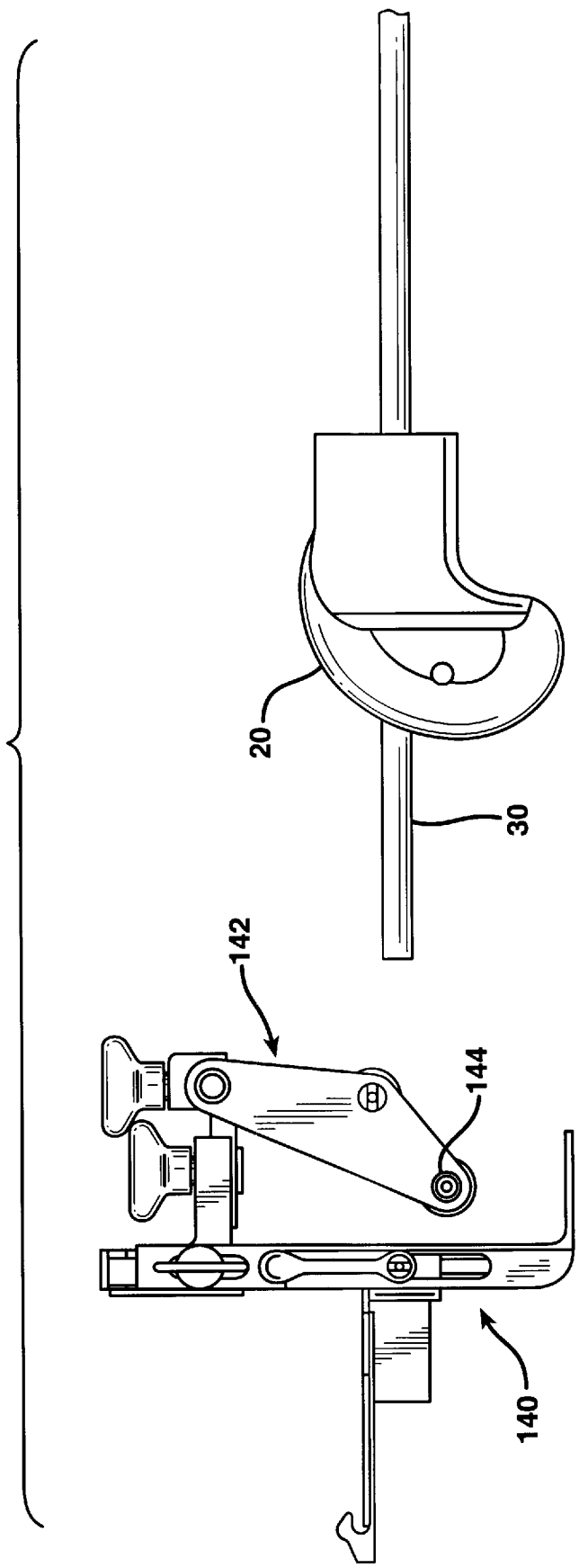

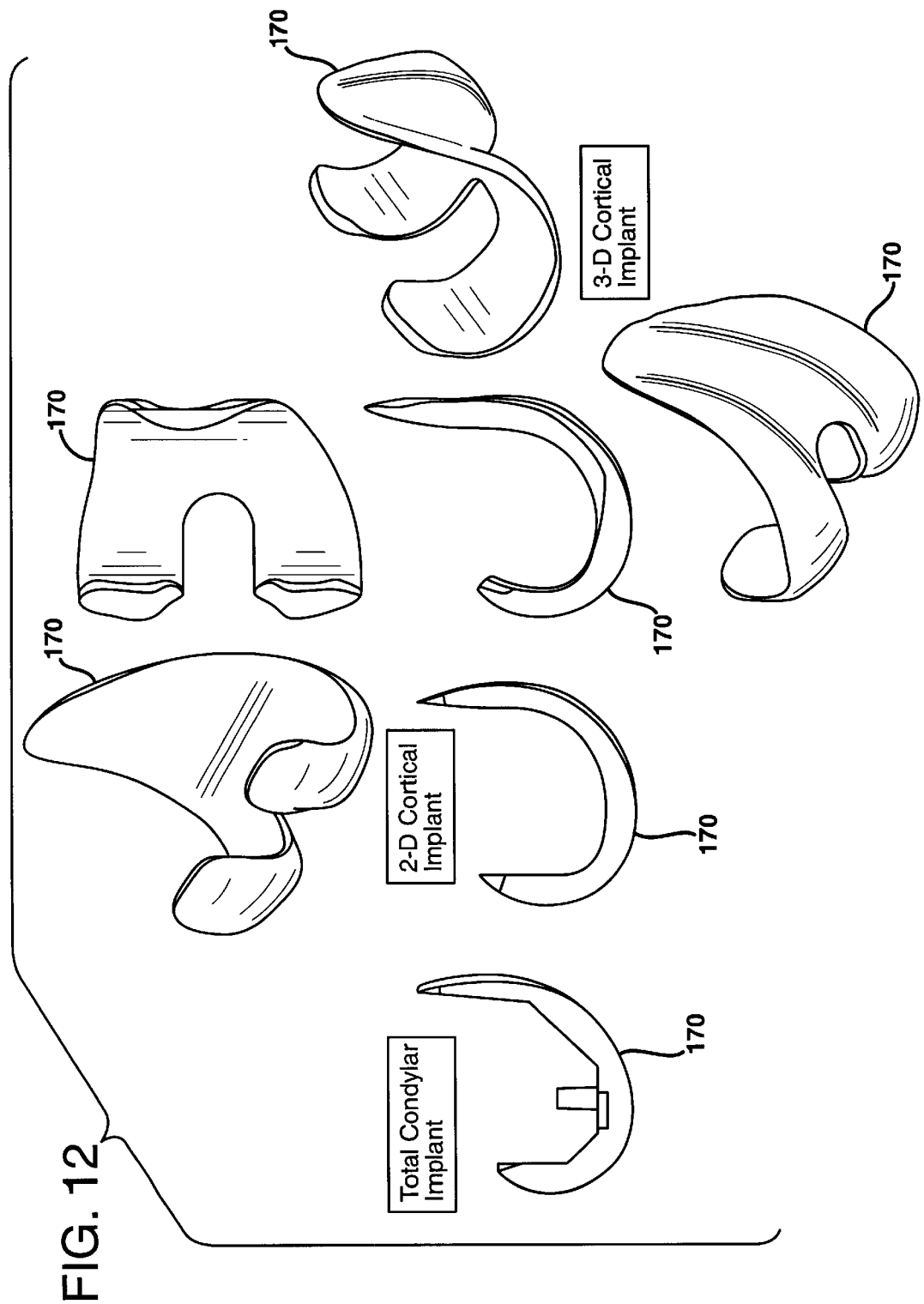

METHODS FOR FEMORAL AND TIBIAL RESECTION

RELATED APPLICATIONS

This application is a continuation-in-part of copending application Ser. No. 09/261,528, filed Mar. 3, 1999, now U.S. Pat. No. 6,197,064, which was a continuation of Ser. No. 08/892,286 filed Jul. 14, 1997, now U.S. Pat. No. 5,879,354, which was a divisional of U.S. patent application Ser. No. 08/649,465, filed May 17, 1996, now U.S. Pat. No. 5,755,803, which was a continuation-in-part application of U.S. patent application Ser. No. 08/603,582, filed Feb. 20, 1996, now U.S. Pat. No. 5,810,827 which was a continuation-in-part application of U.S. patent application Ser. No. 08/300,379, filed Sep. 2, 1994 by Goldstein, et al., now U.S. Pat. No. 5,514,139, dated May 7, 1996.

U.S. patent application Ser. No. 08/603,582, filed Feb. 20, 1996, now U.S. Pat. No. 5,810,827, is also a continuation-in-part application of U.S. Ser. No. 08/479,363 filed Jun. 7, 1995, now U.S. Pat. No. 5,643,272 which is a continuation-in-part of U.S. patent application Ser. No. 08/342,143, filed Nov. 18, 1994 by Haines, et al., now U.S. Pat. No. 5,597,379, which is a continuation-in-part application of U.S. patent application Ser. No. 08/300,379, filed Sep. 2, 1994, by Goldstein, et al., now U.S. Pat. No. 5,514,139, dated May 7, 1996. U.S. Ser. No. 08/479,363, now U.S. Pat. No. 5,643,272 is also a continuation-in-part of U.S. Ser. No. 08/300,379, now U.S. Pat. No. 5,514,139. U.S. Ser. No. 08/603,582, now U.S. Pat. No. 5,810,872 is also a continuation-in-part application of U.S. Ser. No. 08/342,143 now U.S. Pat. No. 5,597,379 which is a continuation-in-part application of U.S. Ser. No. 08/300,379 now U.S. Pat. No. 5,514,139.

The entire disclosures of these related applications are expressly incorporated herein by reference.

BACKGROUND OF THE INVENTION

1. Field of the Invention

This invention generally relates to methods and apparatus for femoral and tibial resection to allow for the interconnection or attachment of various prosthetic devices.

2. Related Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In Total Knee Replacement a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in Total Knee Replacement for over 30 years. Due to their use of this sub-optimal cutting tool, the instrumentation systems all possess certain limitations and liabilities.

Perhaps the most critical factor in the clinical success of TKA is the accuracy of the implant's placement. This can be described by the degrees of freedom associated with each implant; for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of $\frac{1}{8}^{th}$ or $\frac{3}{16}^{th}$ inch diameter pin or drill placement in the anterior or distal faces of the femur for placement of cutting guides. In the case of posterior referencing systems, the distal resection cutting guide is positioned by drilling two long drill bits into the anterior cortex. As these long drills contact the oblique surface of the femur they very often deflect, following the path of least resistance into the bone. As the alignment guides are disconnected from these cutting guides, the drill pins will 'spring' to whatever position was dictated by their deflected course thus changing their designated, desired alignment to something less predictable and/or desirable. This kind of error is further compounded by the 'tolerance stacking' inherent in the use of multiple alignment guides and cutting guides. Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA for more than 30 years, orthopedic salespeople still report incidences where poor cuts result in significant gaps in the fit between the implant and the bone.

It is an often repeated rule of thumb for orthopedic surgeons that a "Well placed, but poorly designed implant will perform well clinically, while a poorly placed, well designed implant will perform poorly clinically". One of the primary goals of the invention described herein is to eliminate errors of this kind to create more reproducible, consistently excellent clinical results in a manner that requires minimal manual skill on the part of the surgeon.

None of the previous efforts of others disclose all of the benefits and advantages of the present invention, nor do the previous efforts of others teach or suggest all the elements of the present invention.

OBJECTS AND SUMMARY OF THE INVENTION

It is a primary object of the present invention to provide methods and apparatus for femoral and tibial resection.

It is another object of the present invention to provide a method and apparatus for properly, accurately and quickly resecting a bone.

It is also an object of this invention to provide a method and apparatus for properly orienting and locating a resection of a bone.

It is a further object of the present invention to provide a method and apparatus to properly locate and orient the resection apparatus with respect to a bone.

It is another object of the present invention to provide methods and apparatus for femoral and tibial resection which are simple in design and precise and accurate in operation.

It is an additional object of the present invention to provide a method and apparatus to physically remove material from a bone in a pattern dictated by a pattern device and/or the geometry of a cutting device.

It is a further object of the present invention to provide methods and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is a further object of the present invention to provide methods and apparatus for femoral and tibial resection wherein the apparatus can be located on a bone to be cut in a quick, safe and accurate manner.

These objects and others are met by the methods and apparatus for femoral and tibial resection of the present invention. The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A conventional cutting block used with a conventional oscillating saw can also be positioned and interconnected with a femur in a similar manner using the drill guide of the present invention to create medial and lateral holes. A cutting guide can then be attached to the holes. A conventional cutting block can be interconnected with the cutting guide for attachment of the block to the femur. This invention can also be used in connection with a cortical milling system, i.e. a cutting system for providing a curvilinear cutting path and curvilinear cutting profile. Likewise, a tibial cutting guide can similarly be positioned on a tibia with a drill guide.

BRIEF DESCRIPTION OF THE DRAWINGS

Other important objects and features of the invention will be apparent from the following Detailed Description of the Invention taken in connection with the accompanying drawings in which:

FIG. 1B is a side view thereof.

FIG. 5B is a side view thereof.

FIG. 6B is a side view thereof.

FIG. 12 shows a number of perspective and side views of an implant having a curved attachment face.

DETAILED DESCRIPTION OF THE INVENTION

In the process of developing the basic instrumentation concept discussed in parent U.S. Pat. No. 5,514,139, it was necessary to attach the cutting guides to the femur in a very robust manner in order to prevent deflection or movement of the cutting guide during the cutting process. The concept utilized to avoid cutting guide movement involved a cannulated screw which applied opposable compression to the medial and lateral sides of the femur while a fixation nail was driven through the cannulae to complete fixation. In the earliest cadaveric evaluations of the instrumentation, it was noted that the fixation thus attained was robust enough to allow the 'patient' to be lifted from the table using the guide. Somewhat accidentally, it was also noted that the fixation of the guide to the bone in this manner also avoided any errors in cutting guide placement. Since the cannulated fixation screws were brought directly into contact with the bone surfaces, the moment arm the pins could be subjected too was minimized and thus prevented mal-alignment of the cutting guides. The teachings of the related parent applications are generally discussed herein with reference to FIGS. 1–5.

Figure 1A:
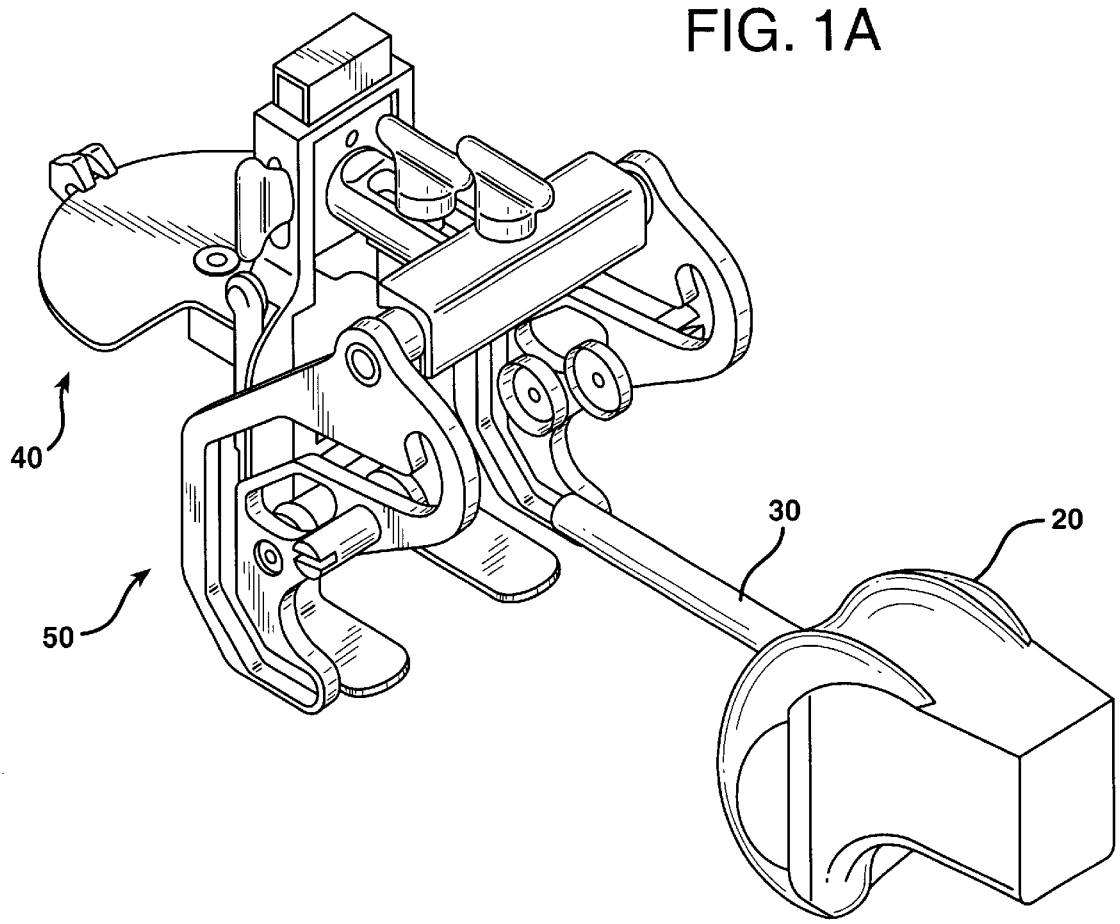
FIG. 1A is a perspective view of an embodiment of a femoral resection apparatus having cutting guides.
Figure 2A:
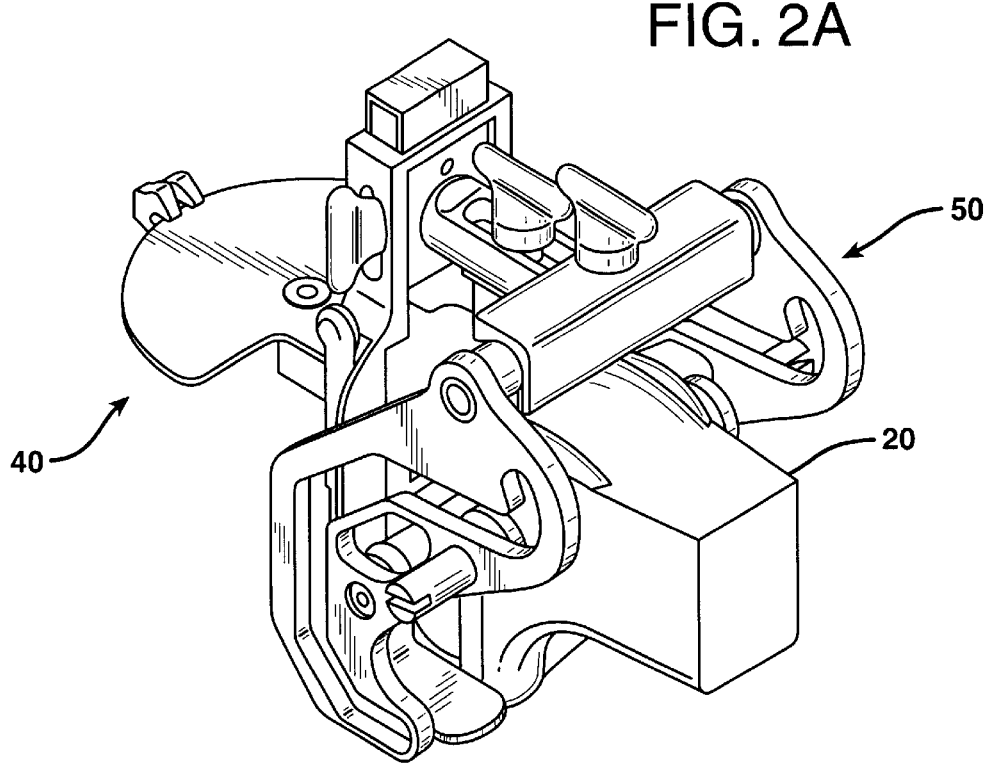
FIG. 2A is a perspective view of the apparatus shown in FIG. 1 affixed to a femur to be resected.
Figure 2B:
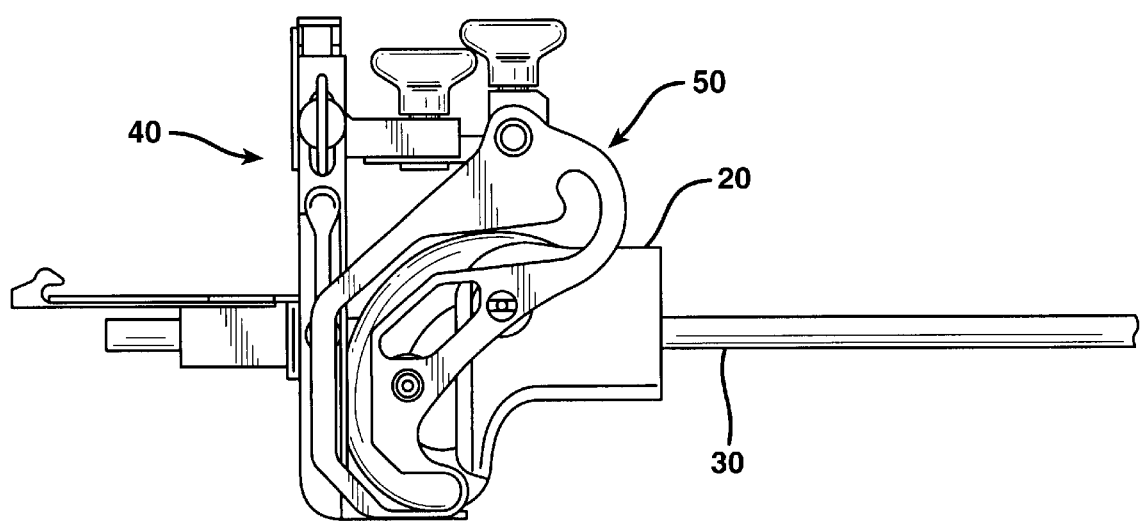
FIG. 2B is a side view thereof.
Figure 3A:
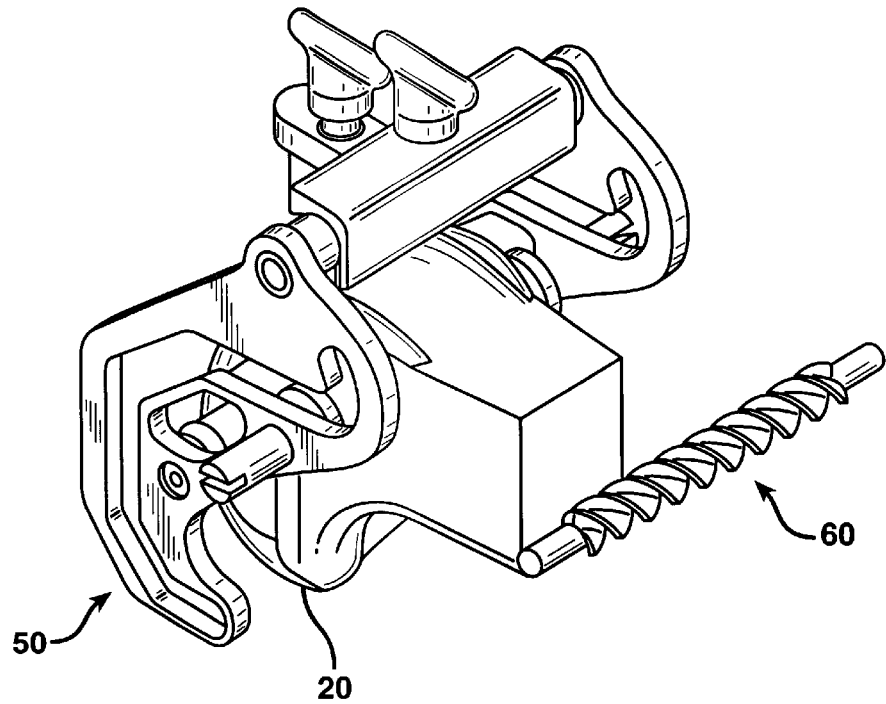
FIG. 3A is perspective view of the cutting guide portion of the femoral resection apparatus shown in FIG. 1 affixed to a femur to be resected, along with a cutting tool.
Figure 3B:
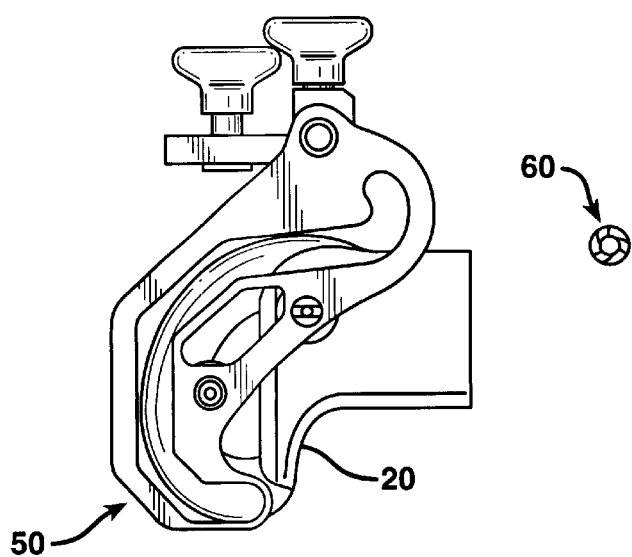
FIG. 3B is a side view thereof.
Figure 4:
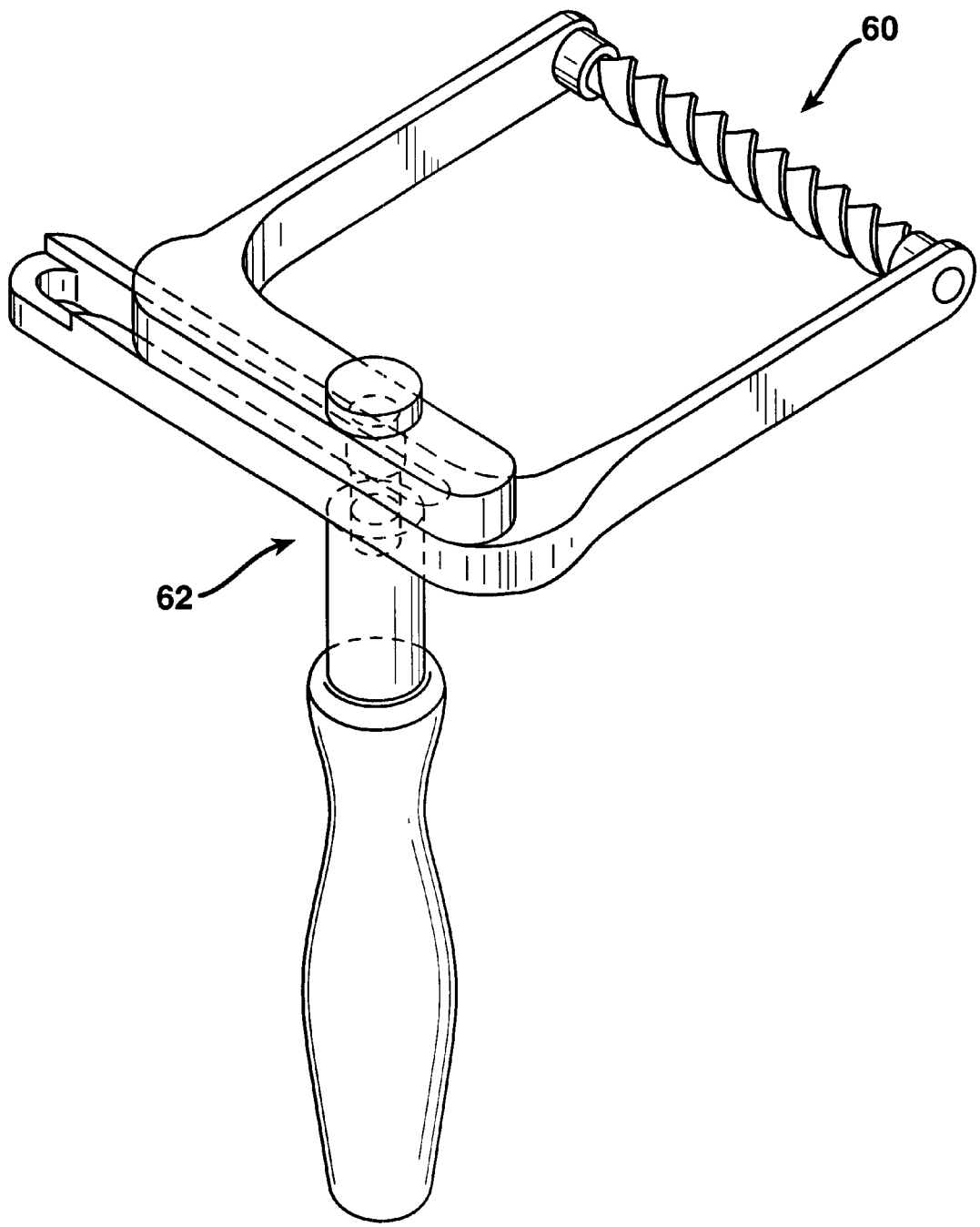
FIG. 4 is a perspective view of a cutting tool and guide handle for resecting a femur.
Figure 5A:
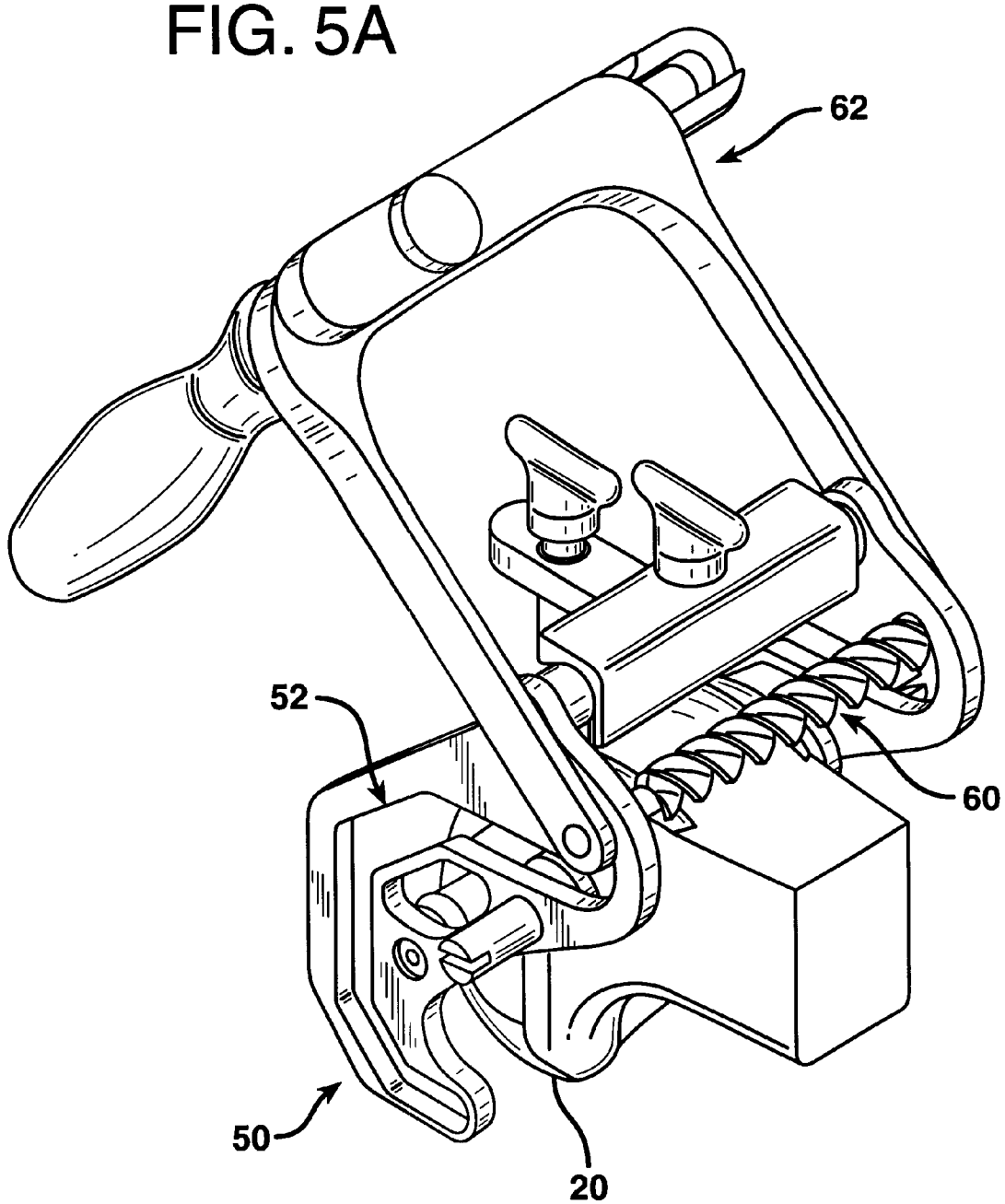
FIG. 5A is a perspective view of the cutting tool interconnected with the cutting guide shown in FIG. 4.
Figure 6A:
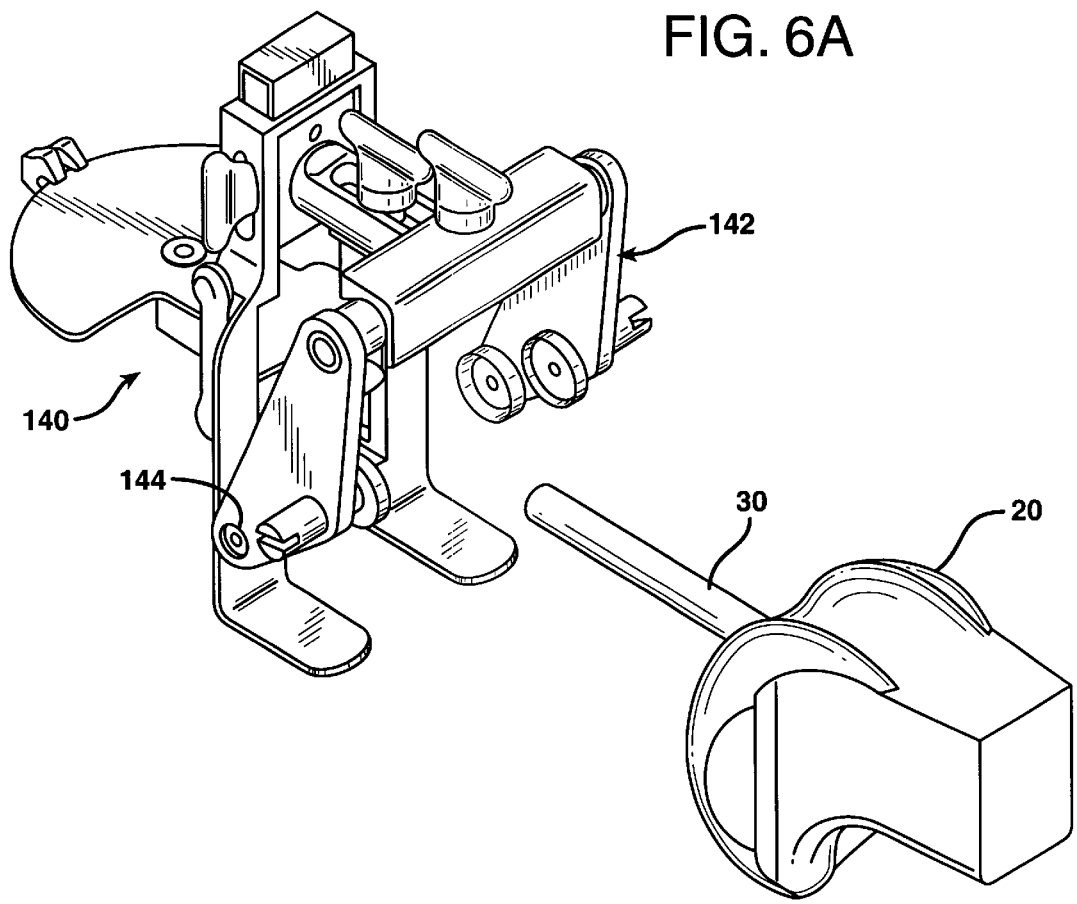
FIG. 6A is a perspective view of the positioning and drill guide apparatus of the present invention, along with a femur to be resected having a intramedullary rod inserted therein.

FIGS. 1A and 1B show the first step in this technique where the intramedullary rod 30 is introduced into the IM canal of the femur 20 while the alignment guide 40 and cutting guide 50 are assembled and then adjusted to the proper relative locations and orientations. FIGS. 2A and 2B show the cutting guide 50 and the alignment guide 40 positioned about the femur 20. The cutting guide 50 is then fixed to the femur 20 using cannulated fixation screws and fixation nails. The alignment guide 40 and intramedullary rod 30 are then removed. FIGS. 3A and 3B show the cutting guide 50 fixed to the distal femur 20 (fixation nails not shown) and the milling tool 60. FIG. 4 shows the milling tool 60 and the milling handle 62. FIGS. 5A and 5B show the milling tool 60 and milling handle 62 properly articulated with the cutting guide 50 prior to initiating the cutting process. The cutting process includes attaching a driver (a DC or AC drill) to the milling tool 60 and to manually direct the milling tool 60 and milling handle 62 through the cutting path 52 of the cutting guide 50.

This technique works well in cadaveric evaluations. Interestingly, there is an inability of the milling tool to cut the collateral ligaments or the posterior cruciate ligament, likely due to the amount of surface area of the milling tool in contact with the ligament. An oscillating sawblade brings finely pointed teeth, teeth whose leading tips are directed at 90 degrees to the ligament fibers, directly into contact with the ligaments, and thus a very small force is required for the very small surface area of the teeth to be forced through the ligament. Another way of stating this is that the local pressure induced by the teeth is very high even when motivated by very small forces due the extremely small surface area of contact between the teeth and the ligament. The milling tool, on the other hand, has teeth which are essentially smooth, and which have much larger areas in contact with the ligament, and are oriented tangentially to the fibers and body of the ligament so that even at the maximum force levels induced by manually pushing the milling handle and milling tool into a ligament (perhaps 25 to 50 lbs.), the ligaments are not cut.

It should be noted that conventional milling was used in evaluations. Conventional milling, in the case of this instrumentation, dictates that the milling bit rotates in the opposite of the direction from the cutting direction to maximize both control during cutting and the smoothness of the resulting surfaces. Climb milling, the opposite of conventional milling, is potentially problematic and may be avoided by utilizing a one way clutch between the milling tool and the drill driving the milling tool thus avoiding even accidental use of climb milling.

FIGS. 6–9 show a variation on the methods and apparatus of the parent applications which improves the accuracy and ease of use of the instruments. FIGS. 6A and 6B show the alignment guide 140 connected to a drill guide 142. The drill guide 142 has hole locators 144 for locating positioning hole(s) in the medial and lateral sides of the femur 20 that correspond to the fixation features (nubs or cannulated screws) of the cutting guide, as will be described.

Figure 7A:
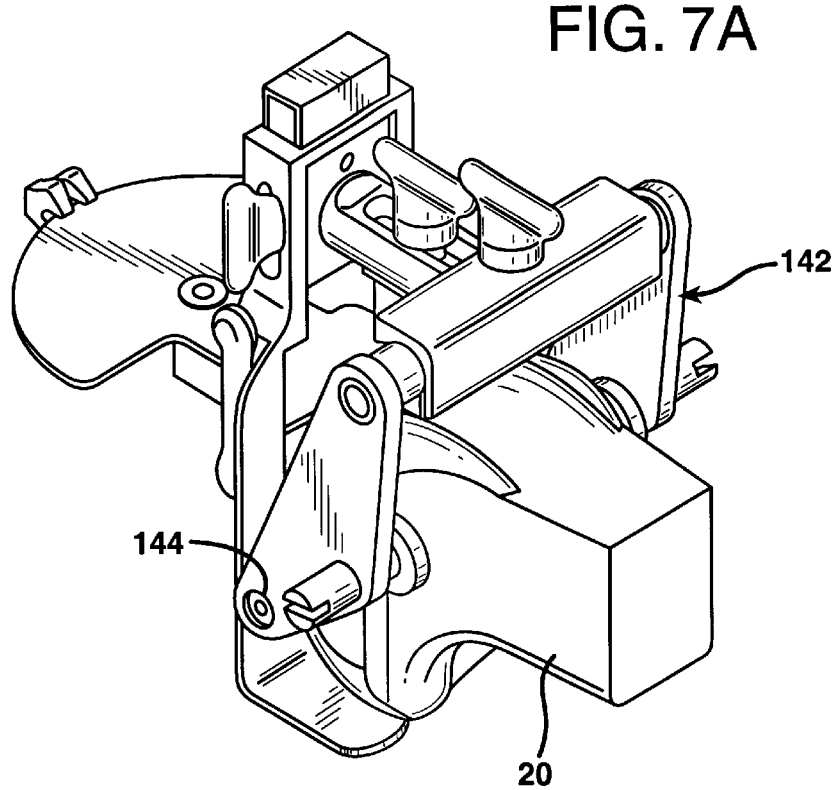
FIG. 7A is a perspective view of the positioning and drill guide apparatus shown in FIG. 6 positioned on a femur to be resected.
Figure 7B:
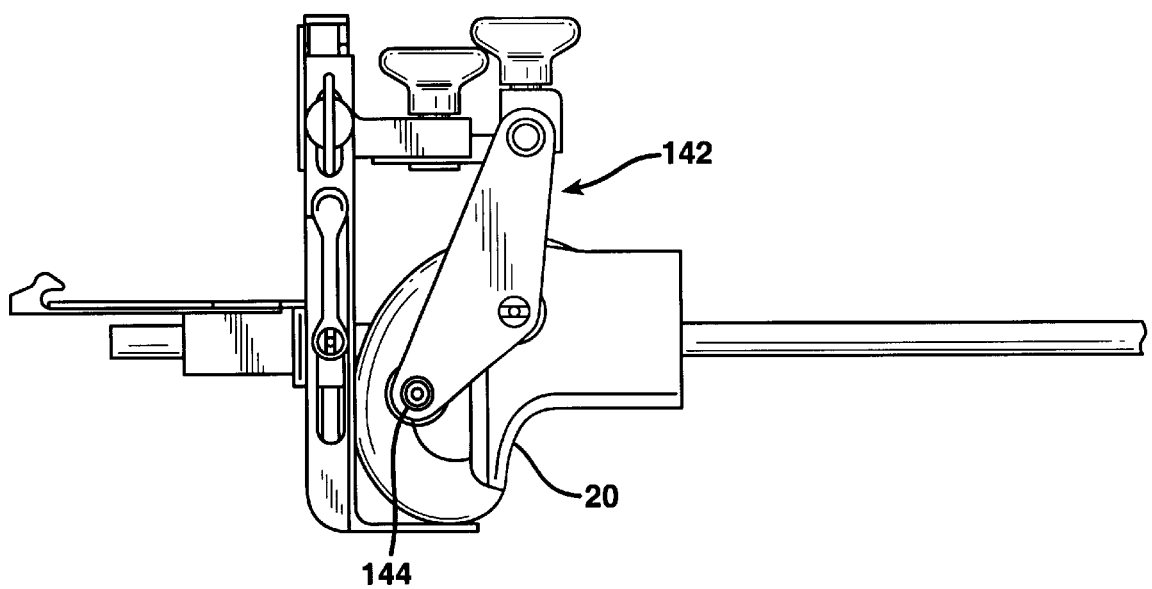
FIG. 7B is a side view thereof.

FIGS. 7A and 7B show the drill guide 142 located about the sides of the distal femur 20. At this point a drill is used to drill through the hole locators 144 in the drill guide 142 to create positioning hole(s) in the medial and lateral sides of the femur. It should be noted that it is possible to place only the distal-most positioning hole in the femur using the drill guide 142, and then to rely on an extramedullary reference to determine the appropriate flexion-extension alignment for the anterior-most fixation point.

Figure 8:
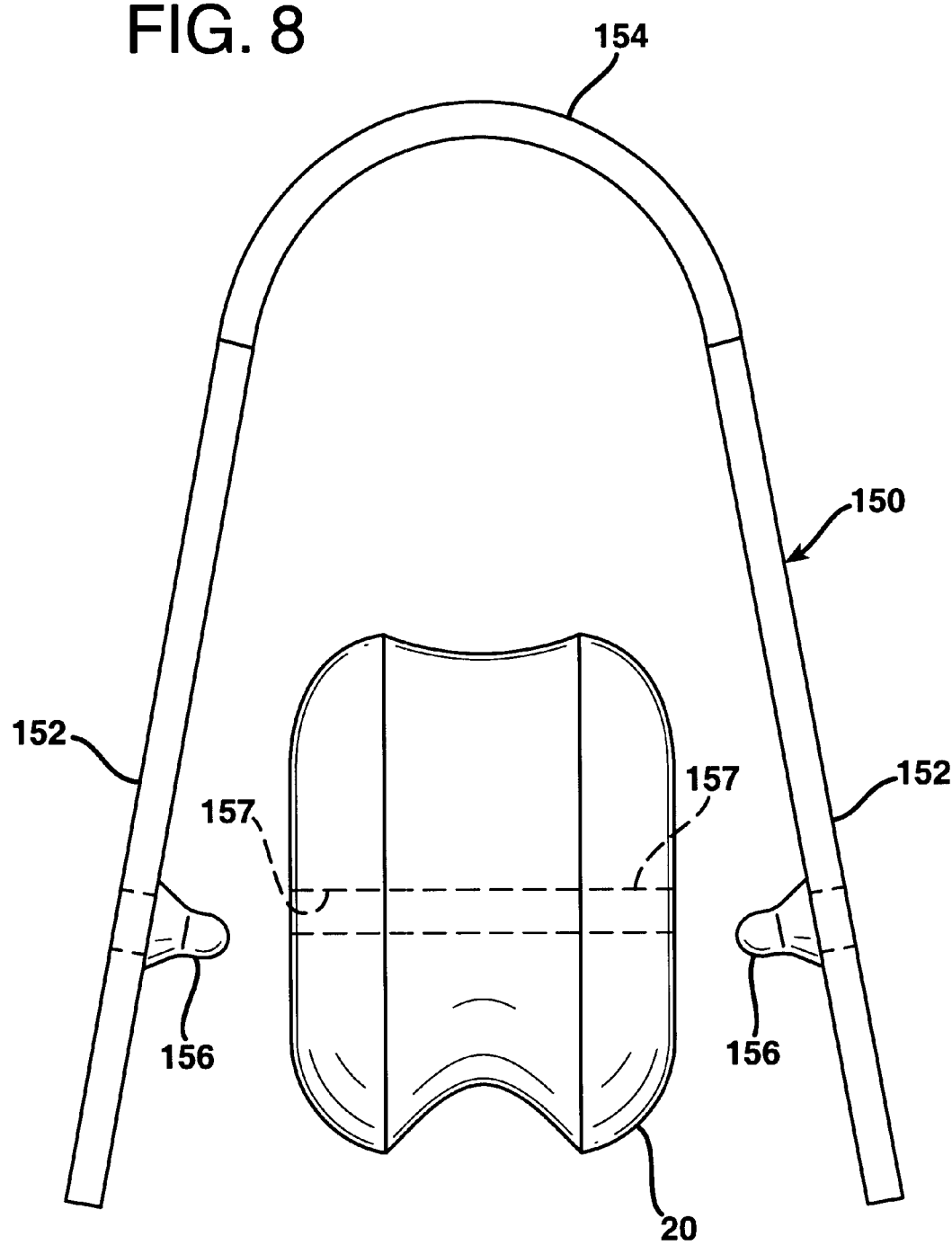
FIG. 8 is a front view of a cutting guide of the present invention positioned for attachment to a femur to be resected.
Figure 9:
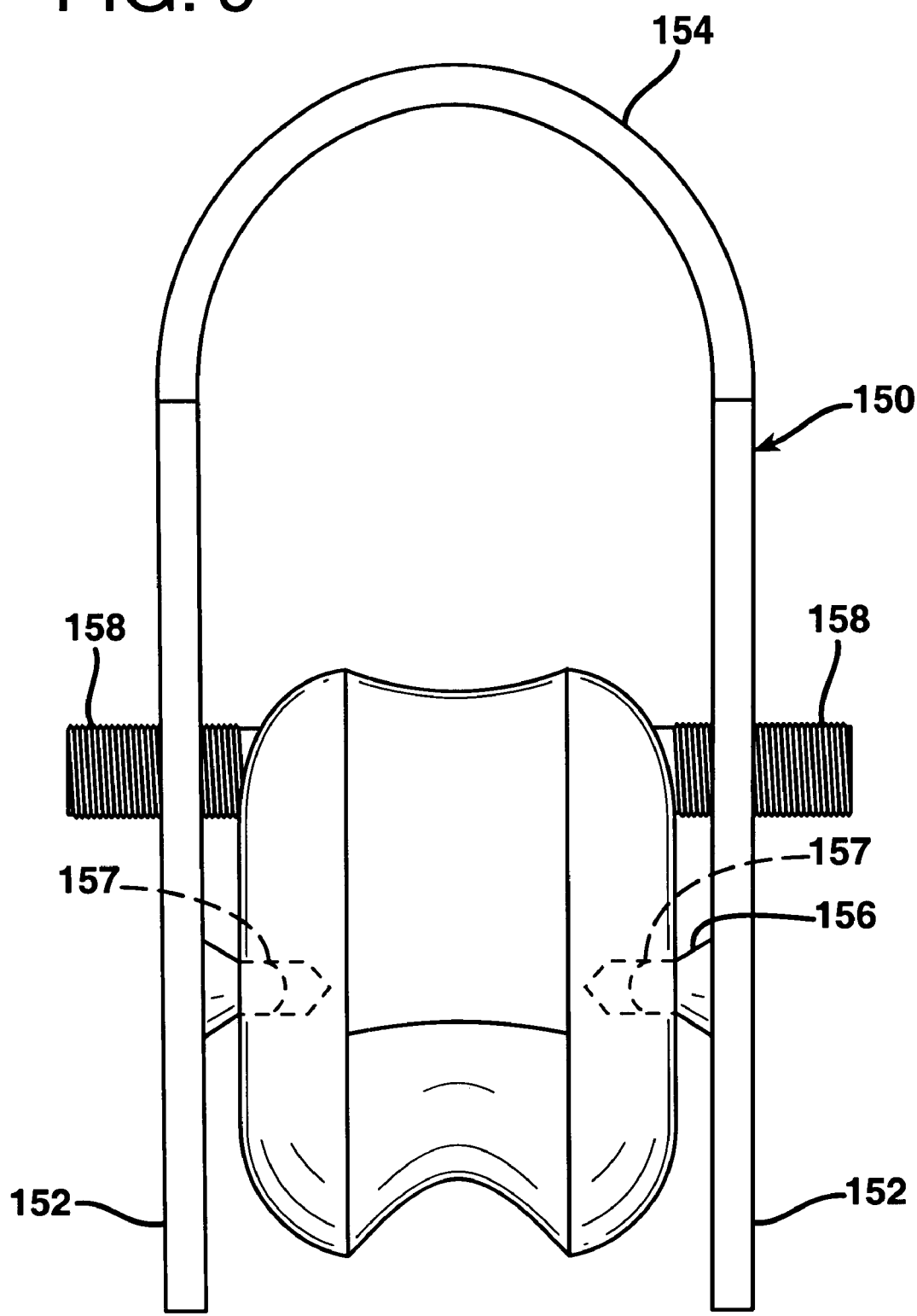
FIG. 9 is a front view of the cutting guide shown in FIG. 8 attached to a femur to be resected.

FIG. 8 shows the cutting guide 150 of this embodiment, having side plates 152 with a cutting path described therein, and an upper bridge 154 interconnecting the cutting plates 152. To position the cutting guide 150 on a femur to be resected 20, the side plates are spread apart to allow for the introduction of fixation nubs 156 into the positioning holes 157 created previously in femur 120. FIG. 9 shows the fixation nubs 156 engaged in the positioning holes 157, and additionally, cannulated fixation screws 158 fixed to the medial and lateral sides of the femur. The step of cutting the distal femur 20 is essentially identical to the techniques shown in FIG. 5.

Figure 10:
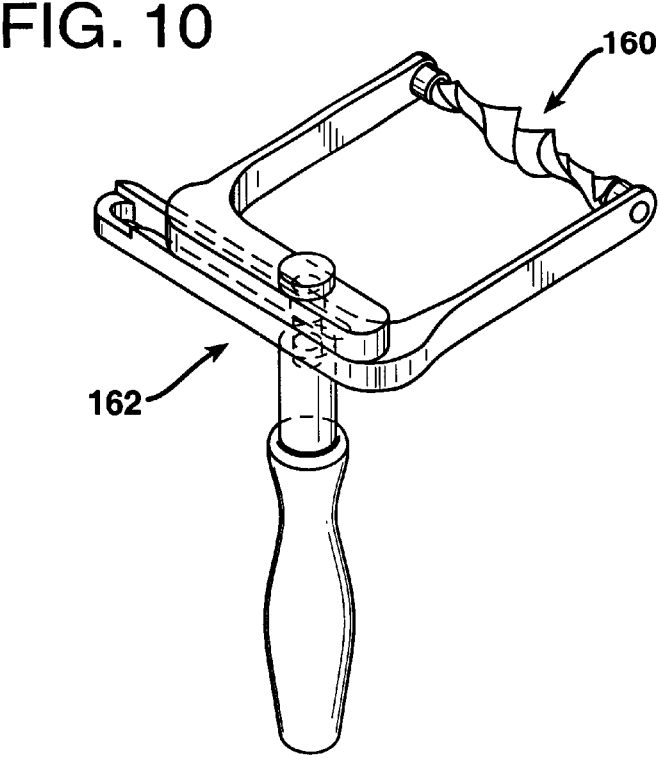
FIG. 10 is a perspective view of a cutting tool and handle wherein the cutting tool has a curvilinear profile.
Figure 11:
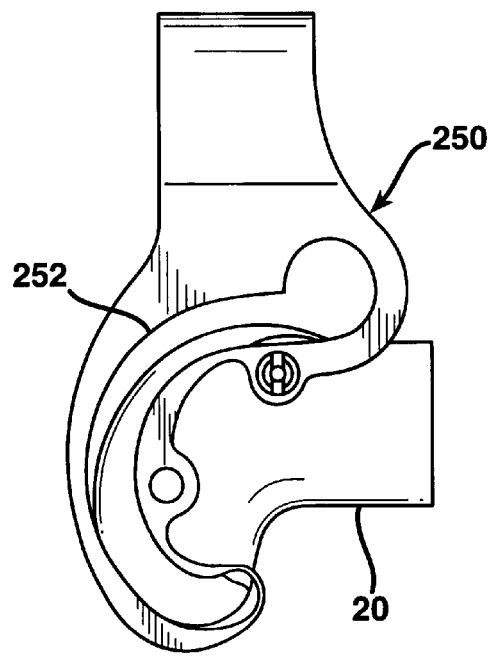
FIG. 11 is a side view of a cutting guide having a curved cutting path attached to a femur to be resected.

FIG. 10 shows a milling tool 160 and handle 162 wherein the cutting blade has a curvilinear profile instead of a linear profile. This allows for shaping the profile of the resection. FIG. 11 shows a cutting guide 250 with a curved cutting path 252, so that a curved cutting path can be used to resect the femur. Using the cutting guide 250 with the curved cutting path 252, together with the curvilinear profile milling tool 160 shown in FIG. 10 allows for the resected femur 20 to have a curved profile and a curved path. Shown in FIG. 12 are examples of a cortical femoral components 170 with linear paths, with curved and linear paths, with curved paths, and with curved paths and curved profiles.

Figure 13B:
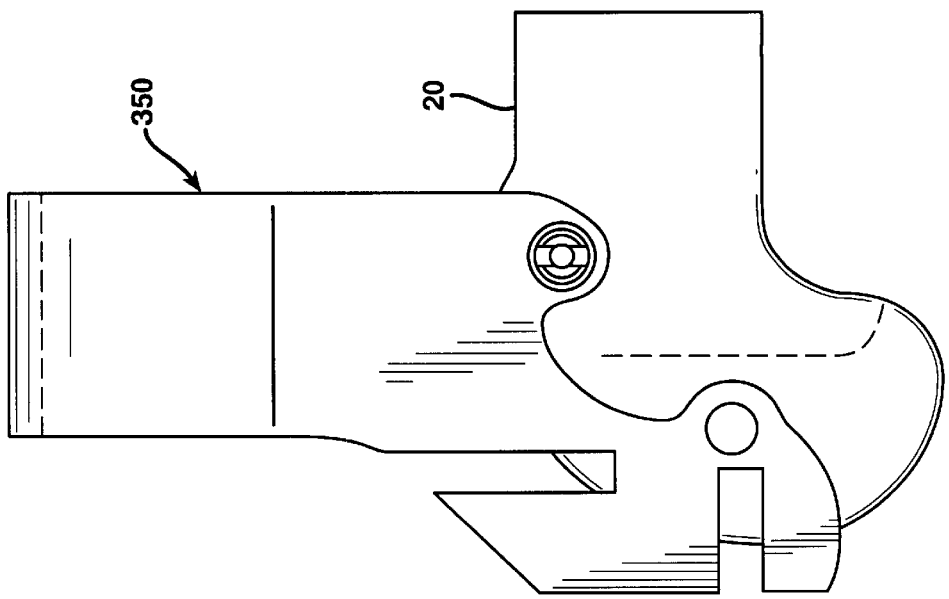
FIGS. 13A and 13B show front and side views of a cutting guide for positioning a cutting block for use with an oscillating saw for resecting a femur.
Figure 13A:
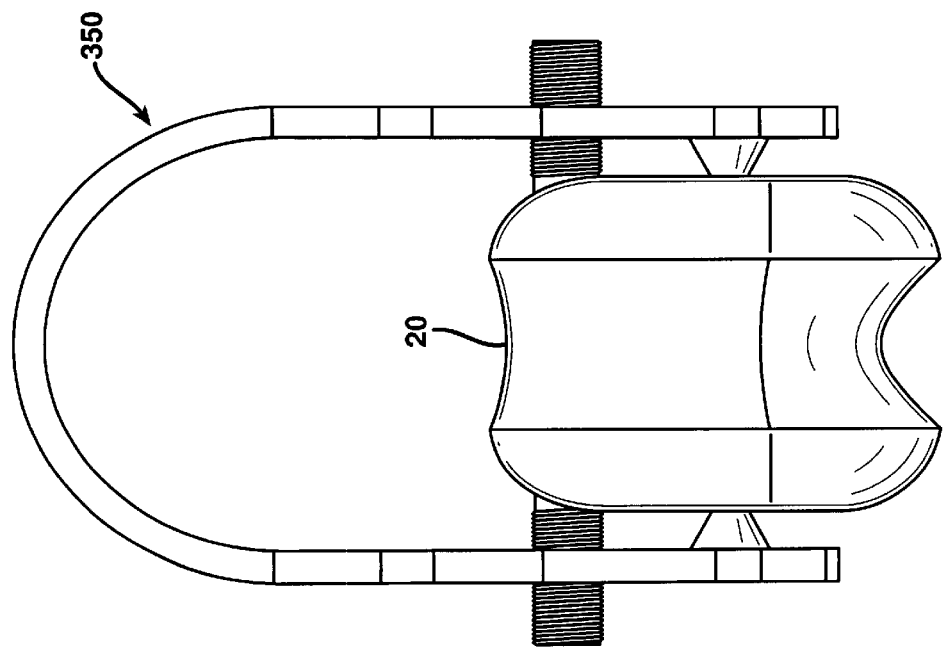
Figure 14B:
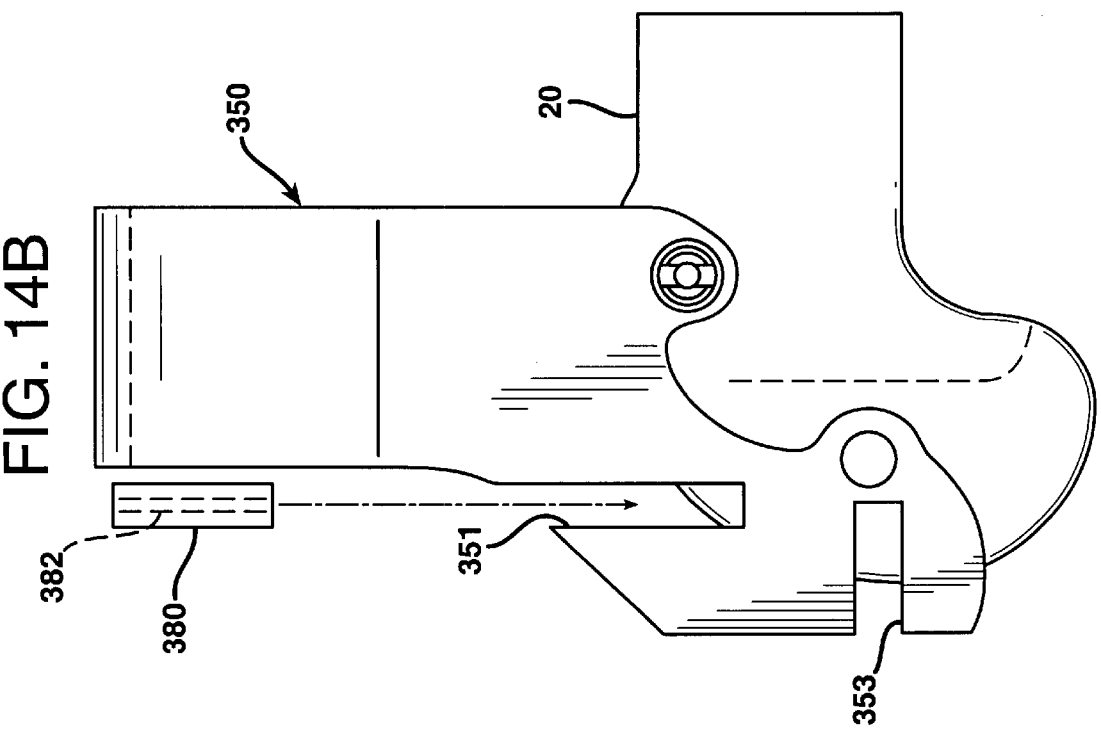
FIGS. 14A and 14B show front and side views of a distal cutting guide for use with the cutting guide shown in FIG. 14.
Figure 14A:
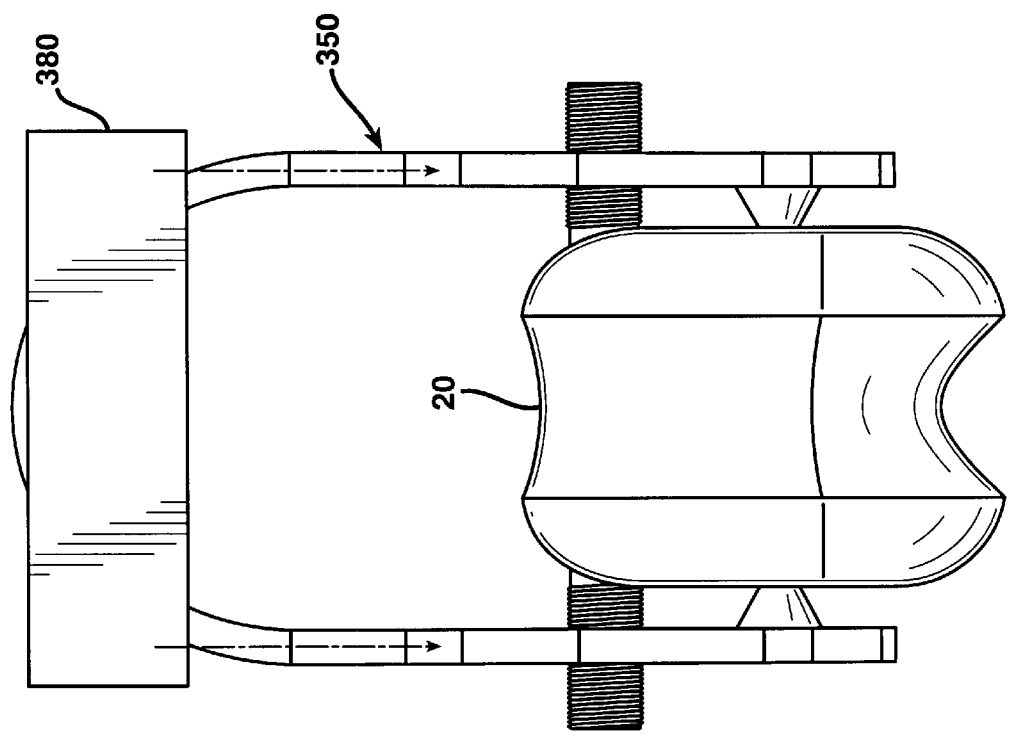
Figure 15A:
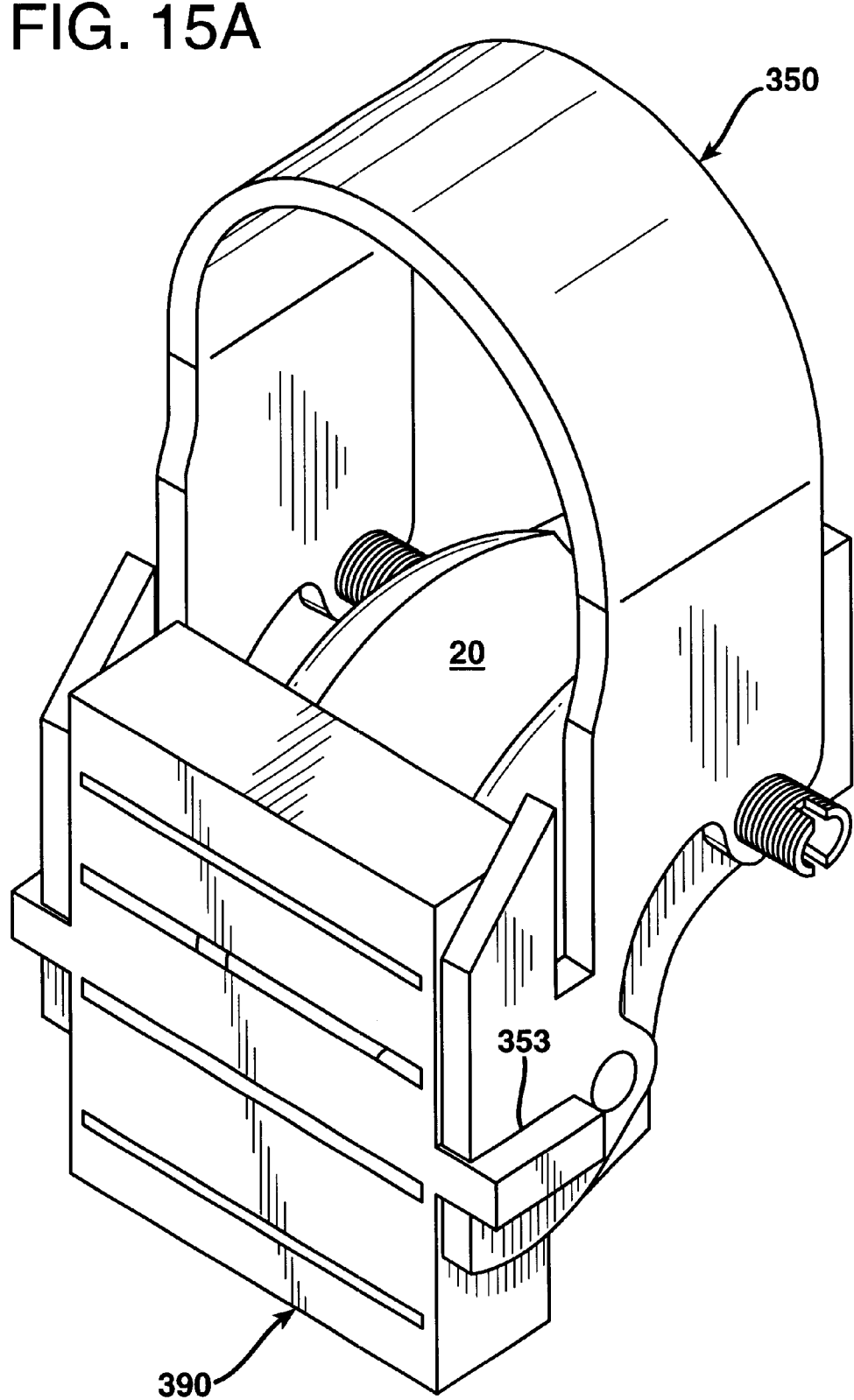
FIG. 15A is a perspective view of a cutting block interconnected with the cutting guide shown in FIG. 14, and FIGS. 15B and 15C are side and front views thereof
Figure 15C:
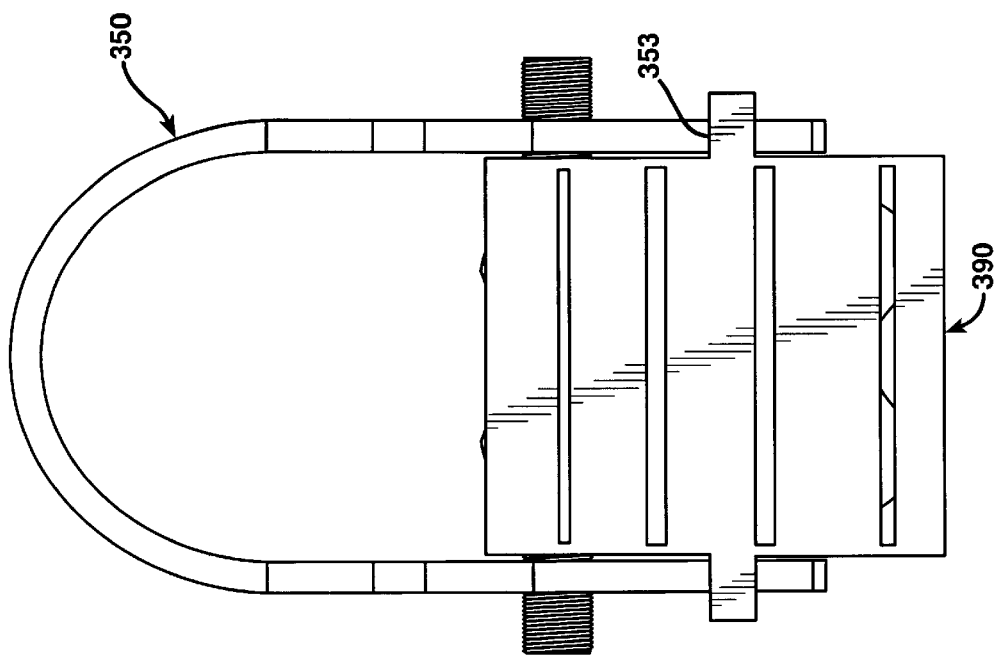
Figure 15B:
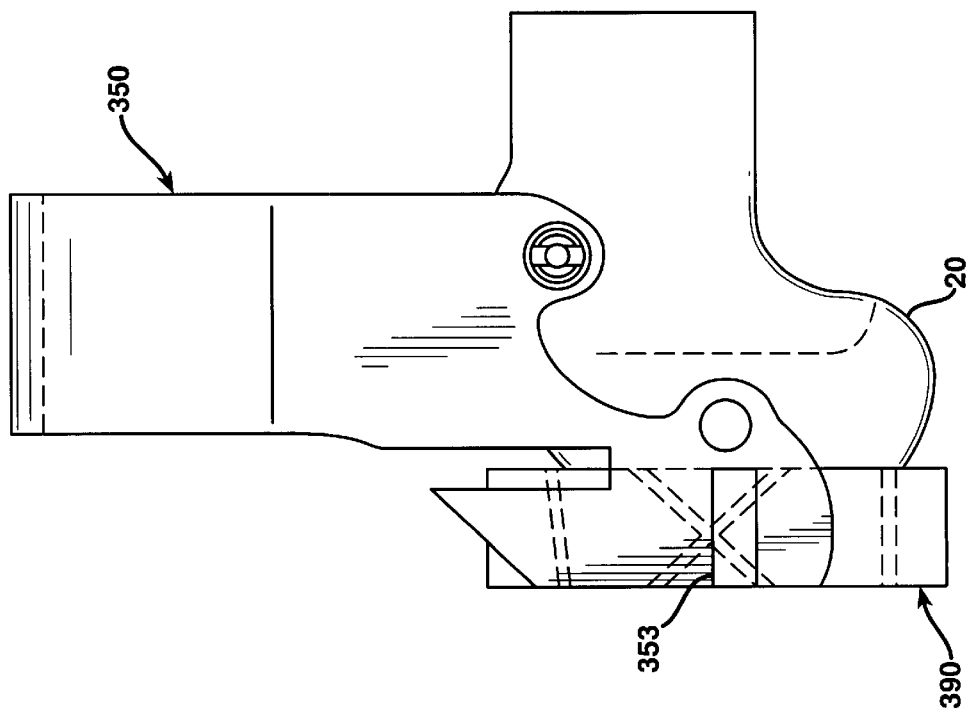

Referring now to FIGS. 13–15, it can be seen that similar techniques can be applied to the use of an oscillating sawblade and a conventional cutting block. FIGS. 13A and 13B show a modified cutting guide 350 attached to the distal femur 20 in a manner similar to the milling cutting guide 150 shown in FIG. 9. FIGS. 14A and 14B show a distal resection cutting guide 380 being attached to the cutting guide 350 by positioning the distal resection cutting guide 380 in slot 351. An oscillating saw is inserted into the slot 382 of the distal resection cutting guide 380 and the distal resection is completed. As shown in FIGS. 15A, 15B and 15C, after the completion of the distal resection and removal of the distal resection cutting guide 380, a 4 in 1 cutting guide block 390 can be inserted into slot 353 until it contacts the distal resection surface of the femur 20. The remaining femoral resections could then be completed as is known in the art. This technique provides and advantage over other 5 in 1 oscillating sawblade techniques in two ways. First, the accuracy of cutting guide placement in significantly improved and second, the leading edges of the sawblade slots in the cutting guides may be brought into direct contact with the bone to be cut thus avoiding excessive cantilevering of the sawblade resulting in sub-optimal cuts.

Figure 16:
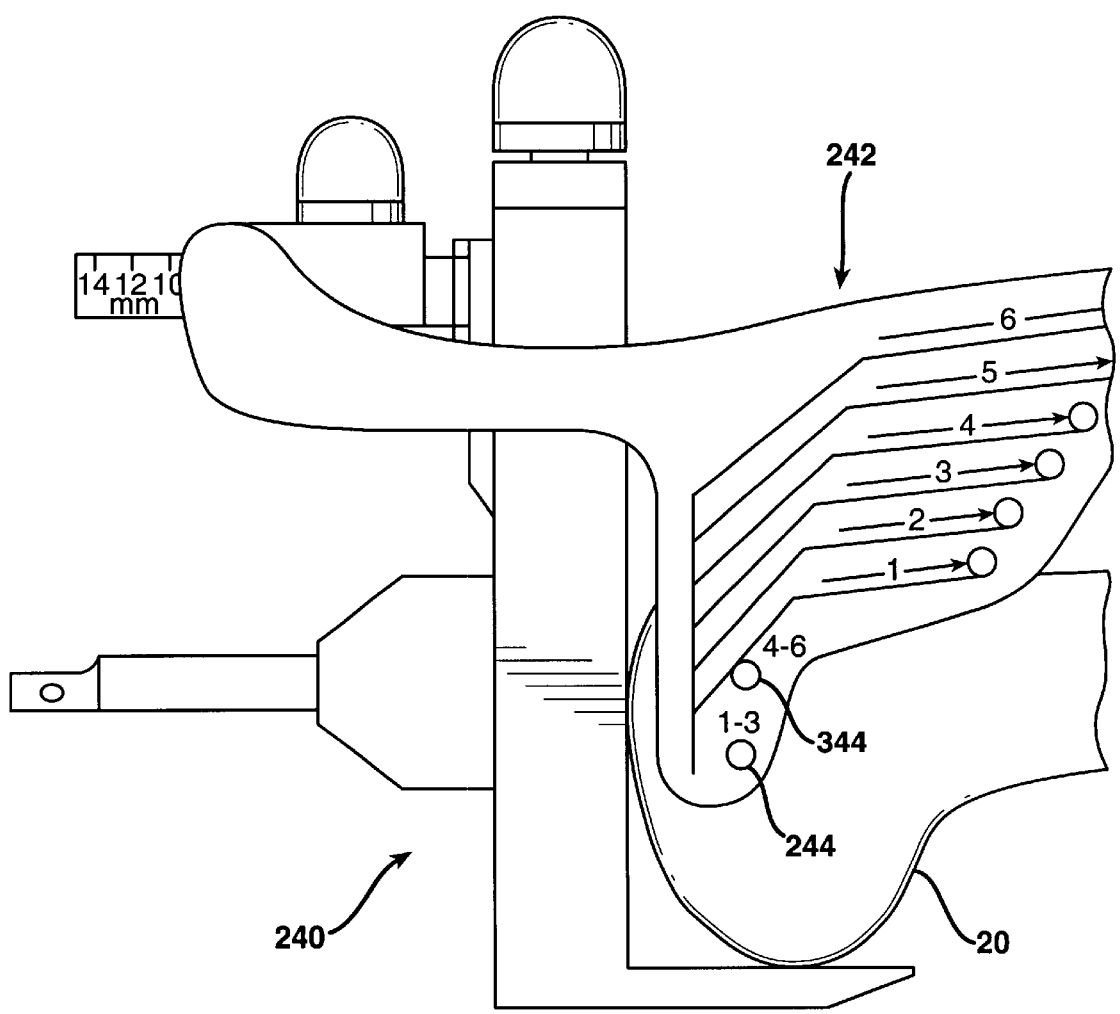
FIG. 16 is a side view of the positioning and drill guide apparatus shown in FIG. 6 showing size markings thereon.
Figure 17:
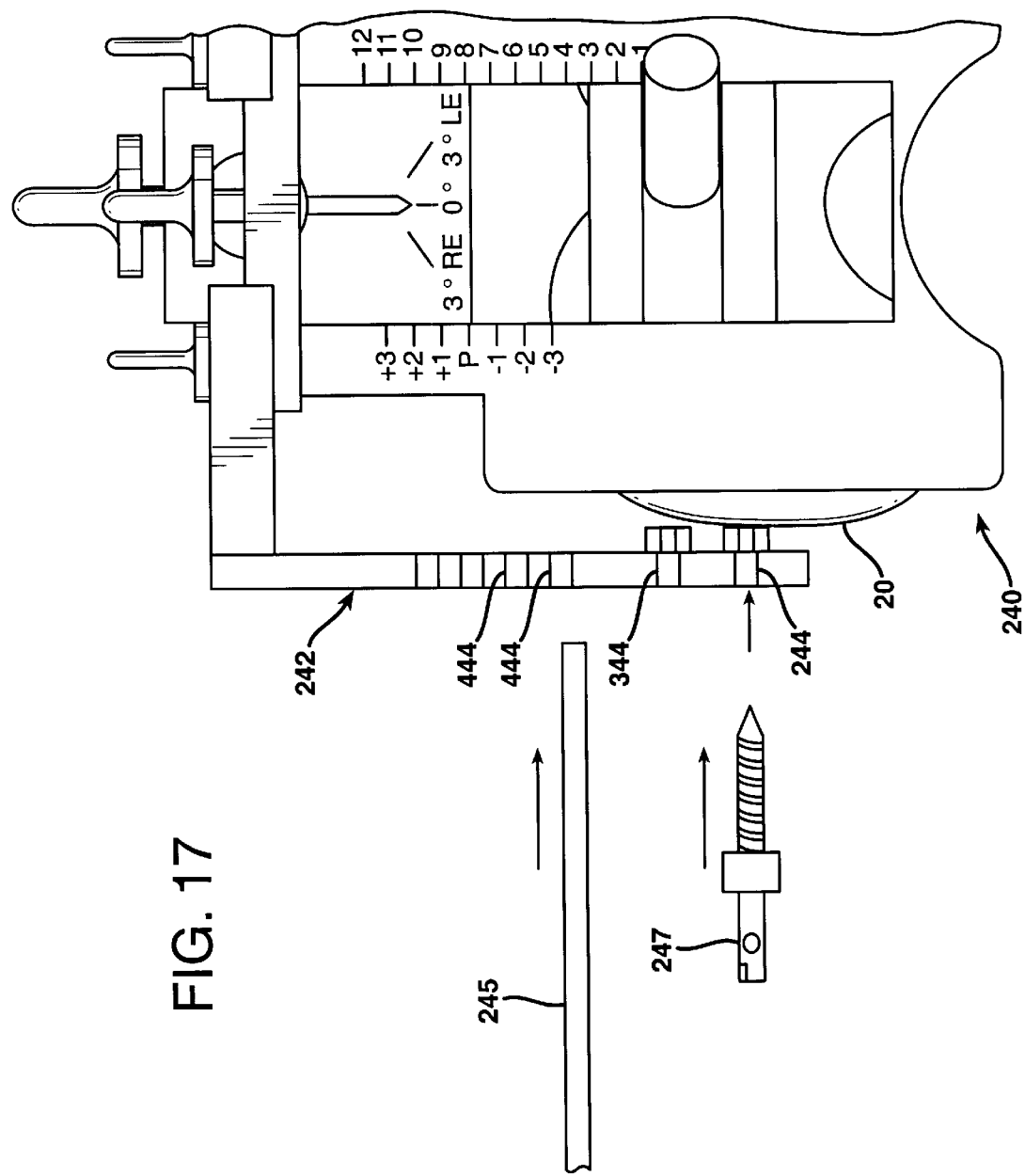
FIG. 17 is a back view thereof.

FIG. 16 is a close up side view of the alignment guide and drill guide shown in FIG. 6. The alignment guide 240 interconnects with the drill guide 242. The drill guide includes a plurality of drill hole locators 244, 344 and size markings. FIG. 17 is a back view of the alignment guide 24 and drill guide 242 shown in FIG. 16. Also shown in FIG. 17 are drill hole locators 244, 344, fixation drill 247 and sizing rod 245 for extending through sizing apertures 444. The sizing rod 245 can be placed from the medial side of the femur to the lateral side in the exact position of the anterior-most tip of the implant corresponding to the size intended for that hole. In this way, the drill holes for cutting guide placement are directly linked to the anterior size reference and the alignment guides reference of the posterior condyles thus minimizing any form of tolerance stacking and allowing for the easy implementation of simultaneous anterior and posterior referencing and adjustment.

Figure 18:
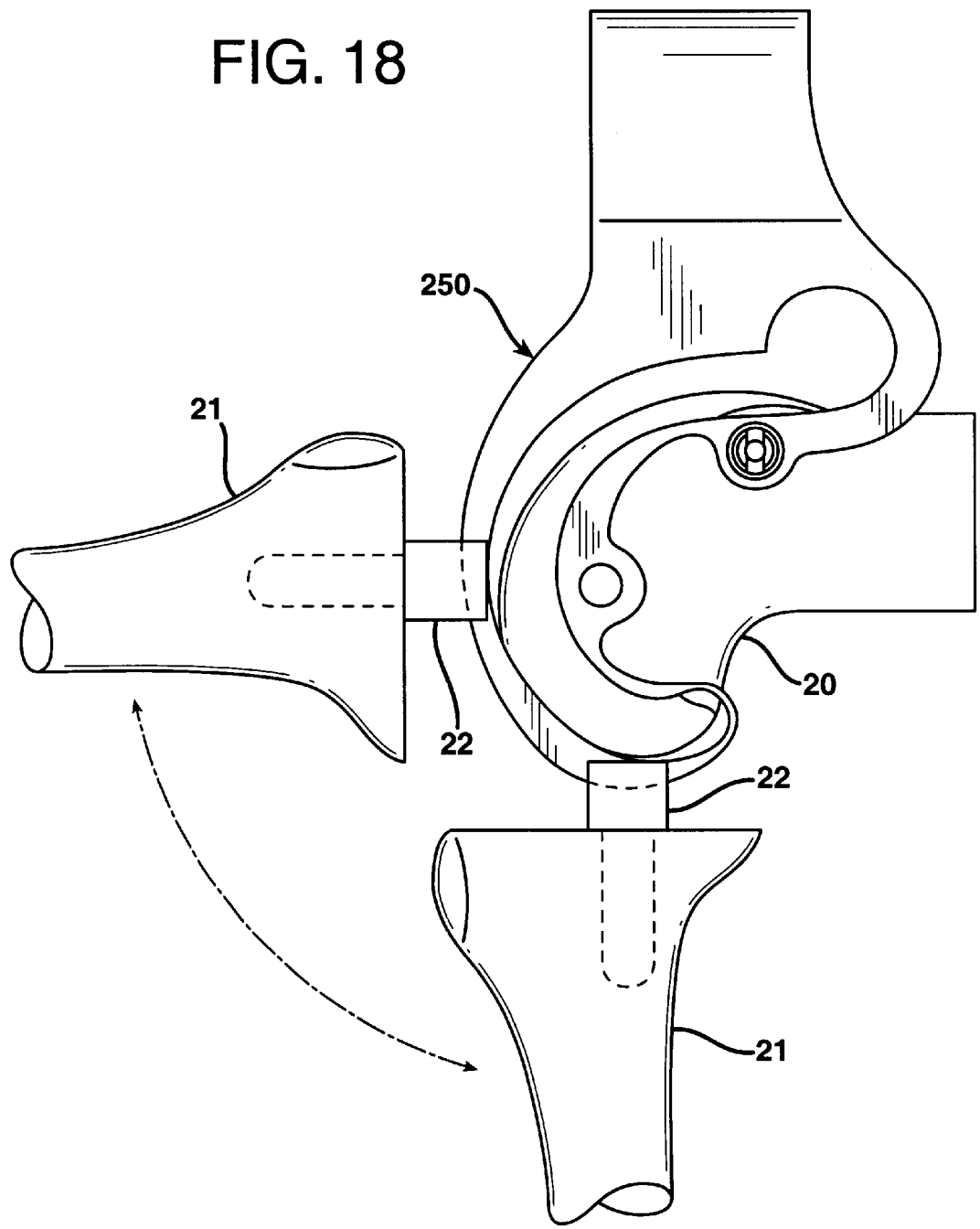
FIG. 18 is a side view of the cutting guide having a curved cutting path shown in FIG. 11 used in connection with ligament balancing.
Figure 19:
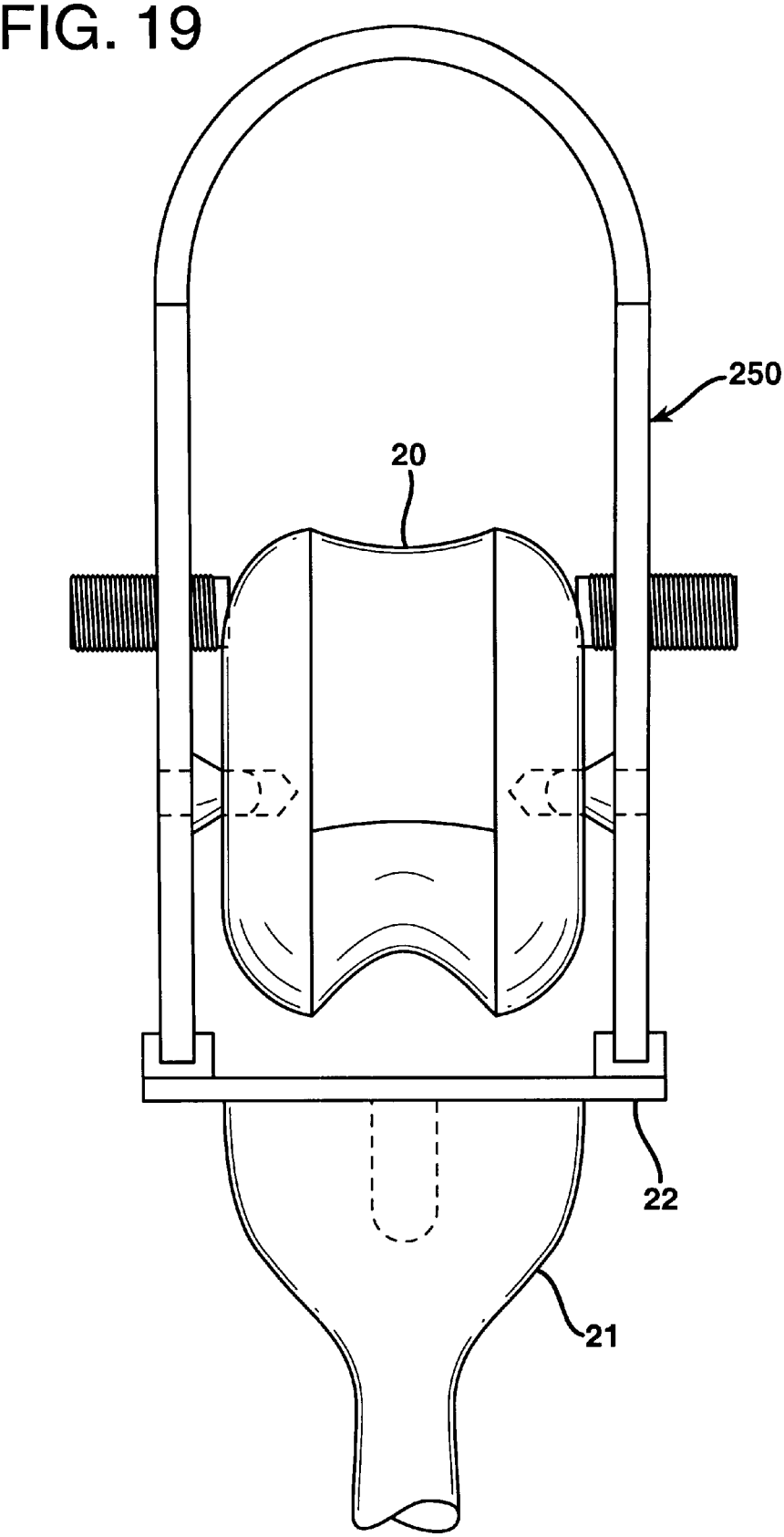
FIGS. 19 and 20 are front and perspective views thereof.
Figure 20:
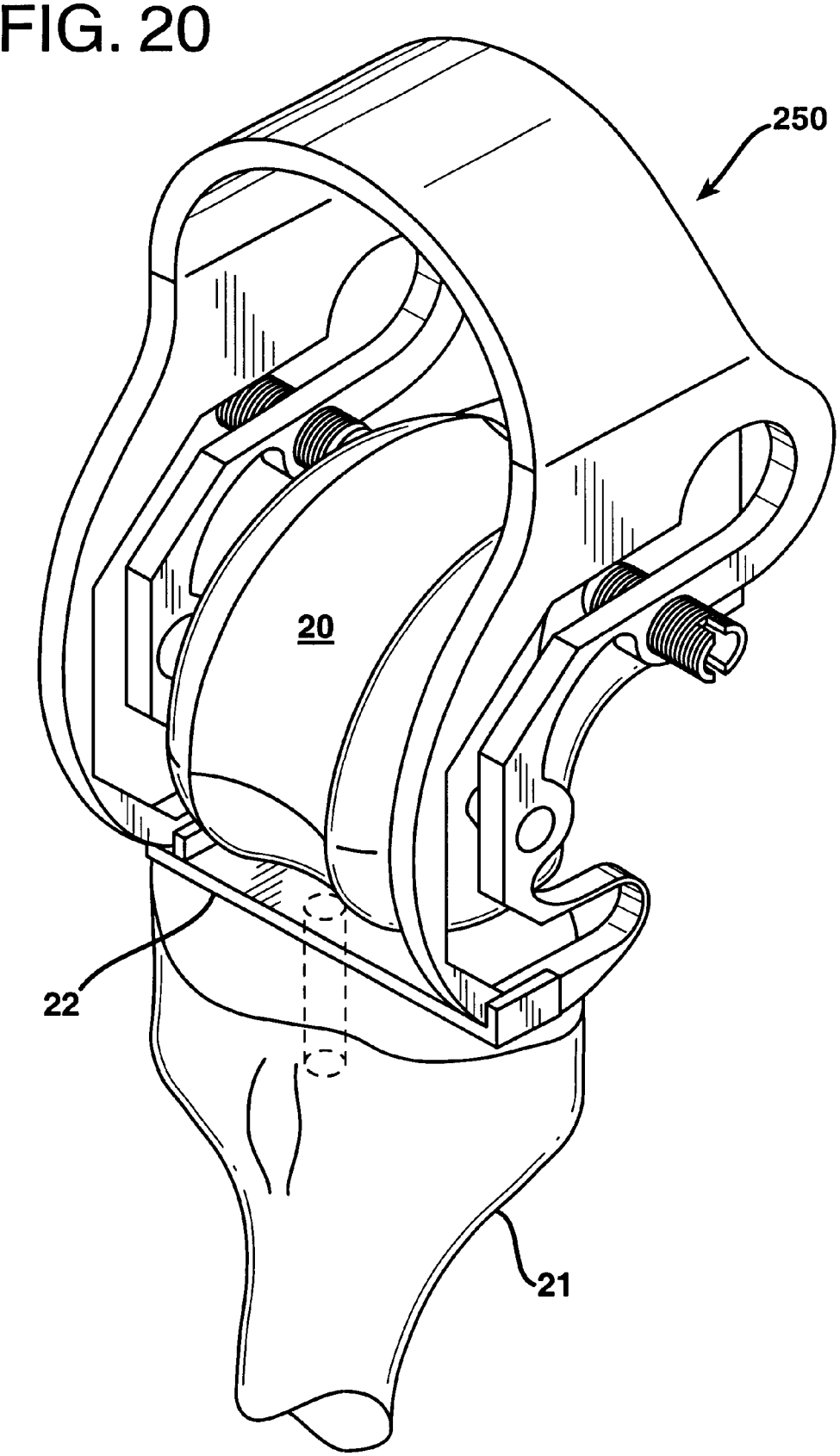

FIGS. 18–20 relate to method of ligament balancing using the cutting guide 250 shown in FIG. 11. Soft tissue balancing for TKA is considered to be crucial in the use of mobile bearing designs. The re-popularization of this technique has spurred the development and commercialization of some very intricate instrumentation systems that are very prone to surgeon misuse due to their complexity. Another drawback of these systems is that they balance the tissues in flexion and extension, but do not allow continuous reference of the soft tissue balance throughout the range of motion similar to that achieved by trial reduction. By creating the edges of the cutting guide 250 (or even a trailing guide including no cutting guide or cutting guide attachment features) in a profile or geometry that simulates the geometry of the implant and having that geometry act or articulate with a referencing means on the cut proximal tibia 21 and reference bar 22 attached thereto, an effective trial reduction of soft tissue balance may be attained prior to any femoral resection.

Figure 21:
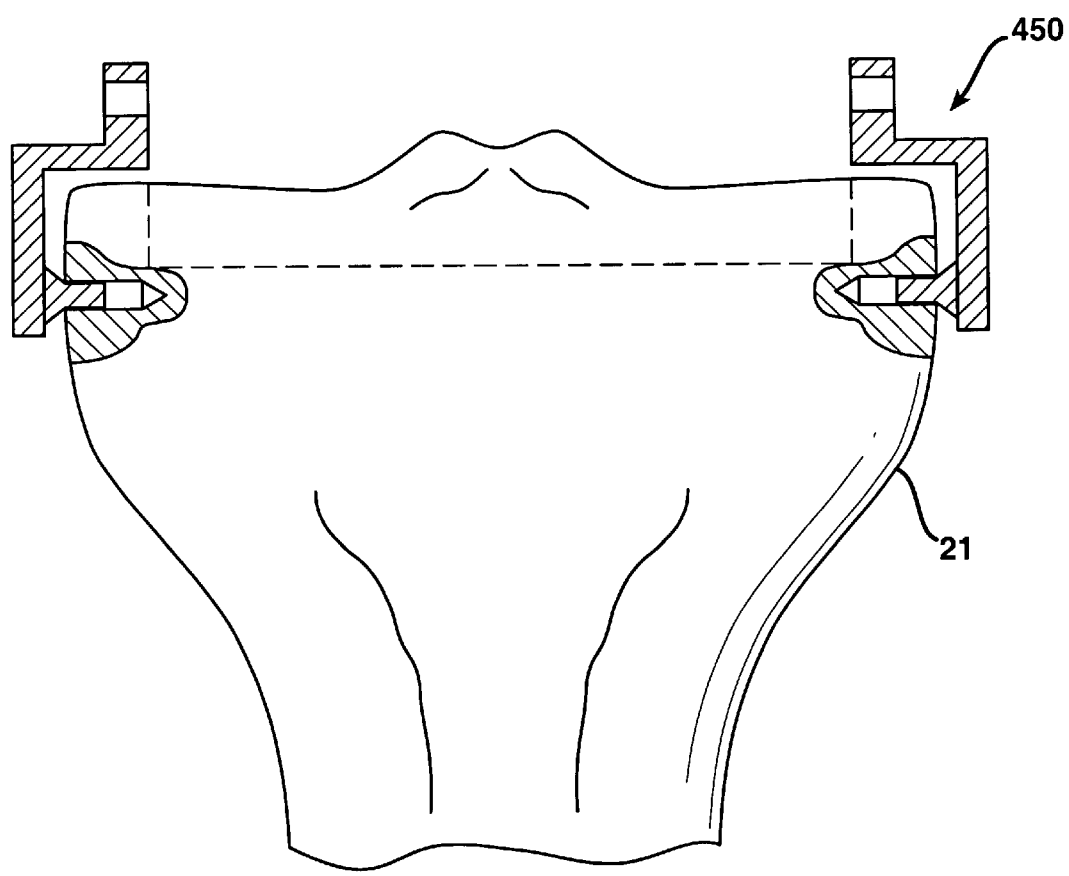
FIGS. 21 and 22 are front and side views of a cutting guide attached to a tibia.
Figure 22:
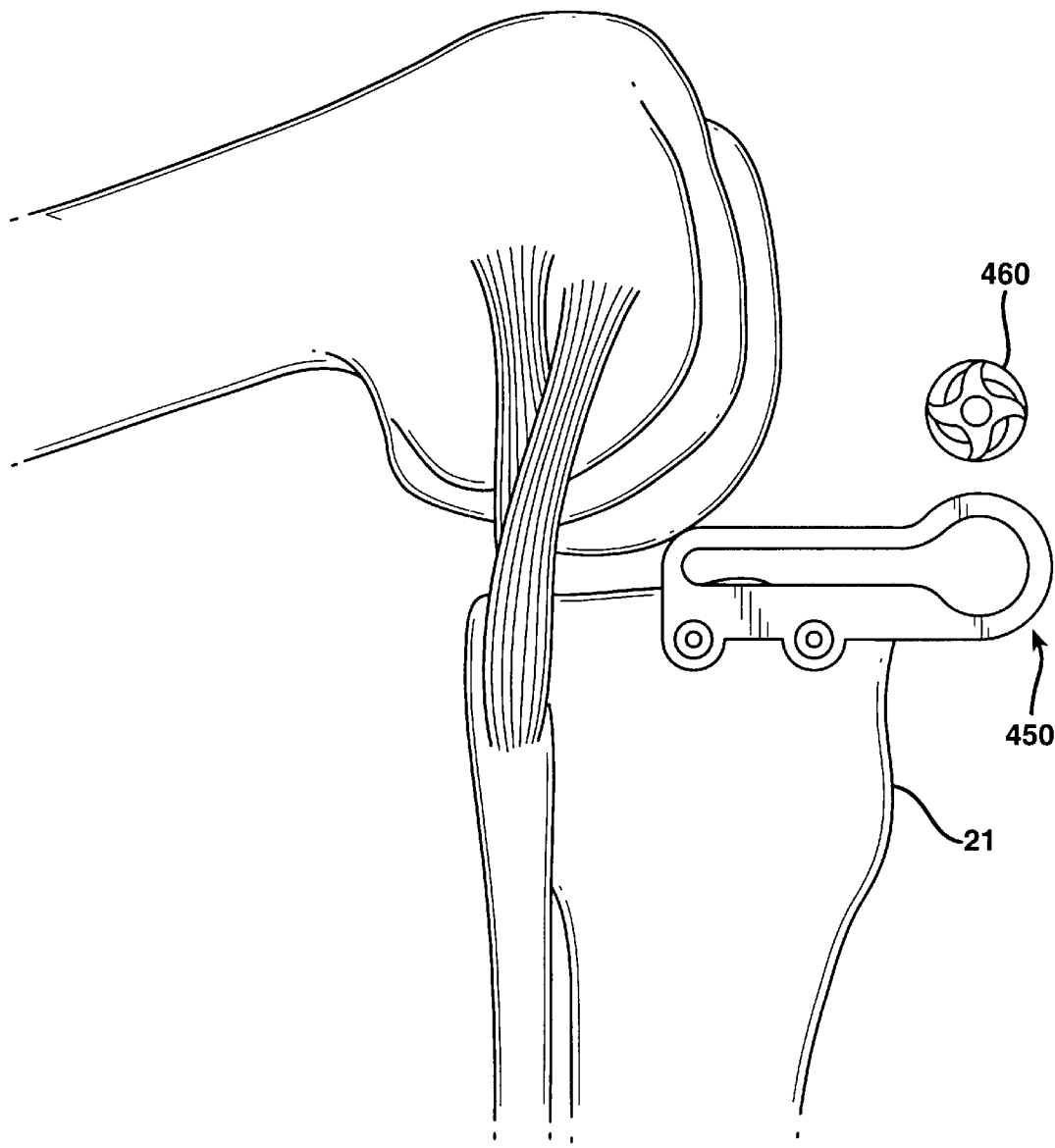

The cutting guide surfaces of the cutting guide need not be coplanar with the surfaces to be created in a bone, but may instead be parallel, but offset. Also the cutting guides may be located over the surfaces of the bone to be cut, but not necessarily located about the sides of the entire bone to be cut. As shown in FIG. 21 a cutting guide 450 may be applied to the tibia or other bones. In addition, the cutting guide shown in FIGS. 21 and 22 is intentional depicted as only being capable of completing the anterior portion of the tibial resection; this is intended to demonstrate that, when planar cuts are desired, the milled surface can be used to guide the remaining resection of an oscillating sawblade thus preserving the accuracy of the milling technique while minimizing the precision errors of the oscillating sawblade.

Modifications of the foregoing may be made without departing from the spirit and scope of the invention. What is desired to be protected by Letters Patents is set forth in the appended claims.

What is claimed is:

1. A method for resecting a femur comprising the steps of:

positioning a drill guide along a femur for locating positioning holes on a femur;

drilling positioning holes in a femur;

spreading apart facing pattern plates interconnected with a bridge to position the plates over medial and lateral sides of a femur;

inserting fixation nubs on the pattern plates into the positioning holes in a femur;

additionally fixing the pattern plates to a femur with fixation hardware; and traversing a cutting tool along a cutting path in the pattern plates.

* * * * *